(12) United States Patent
Funada (10) Patent No.: US 8,736,832 B2
(45) Date of Patent: May 27, 2014

(54) METHOD OF DETECTING SPECIFIC DEFECT, AND SYSTEM AND PROGRAM FOR DETECTING SPECIFIC DEFECT

(75) Inventor: Takeshi Funada, Tokyo (JP)

(73) Assignee: Sumco Corporation, Tokyo (JP)

(*) Notice: Subject to any disclaimer, the term of this patent is extended or adjusted under 35 U.S.C. 154(b) by 238 days.

(21) Appl. No.: 13/428,064

(22) Filed: Mar. 23, 2012

(65) Prior Publication Data

US 2012/0176612 A1 Jul. 12, 2012

(30) Foreign Application Priority Data

Mar. 30, 2011 (JP) ................................. 2011-076376

(51) Int. Cl.
*G01N 21/956* (2006.01)
(52) U.S. Cl.
USPC .................. 356/237.5; 356/237.2; 356/237.4; 356/237.6
(58) Field of Classification Search
CPC .......... G01N 21/9501; G01N 21/9503; G01N 21/9505; G01N 21/9515; G01N 21/958; G01N 22/02
USPC ........................................... 356/237.2–237.6
See application file for complete search history.

(56) References Cited

U.S. PATENT DOCUMENTS

| 7,330,042 | B2* | 2/2008 | Fukazawa et al. | ........ 324/762.01 |
| 2003/0155927 | A1* | 8/2003 | Pinto et al. | .................... 324/501 |
| 2005/0004774 | A1* | 1/2005 | Volk et al. | ..................... 702/108 |
| 2005/0072945 | A1* | 4/2005 | Fukazawa et al. | ........ 250/559.45 |
| 2009/0105990 | A1* | 4/2009 | Shibuya et al. | ............... 702/183 |

FOREIGN PATENT DOCUMENTS

CA 100365790 8/2006

* cited by examiner

*Primary Examiner* — Tarifur Chowdhury
*Assistant Examiner* — Isiaka Akanbi
(74) *Attorney, Agent, or Firm* — Thomas J. Engellenner; Reza Mollaaghababa; Pepper Hamilton LLP (57) ABSTRACT

The present invention provides a detection method which allows specific defects that would occur on a wafer surface to be detected more reliably. A method of detecting a specific defect of the present invention includes the steps of: acquiring a light point map which is in-plane position information of a light point detected in a position corresponding to a defect on a surface of a wafer by irradiating the surface of the wafer with light (S101); specifying a determination region where a specific defect is expected to be formed and a reference region which is a given region other than the determination region in the light point map, and calculating a ratio of a light point density of the determination region to a light point density of the reference region (S102); and determining whether or not the specific defect is formed based on the calculated ratio (S103).

9 Claims, 11 Drawing Sheets

METHOD OF DETECTING SPECIFIC DEFECT, AND SYSTEM AND PROGRAM FOR DETECTING SPECIFIC DEFECT

TECHNICAL FIELD

The present invention relates to a detection method, a detection system, and a detection program for detecting specific defects which would occur on a wafer surface. The present invention particularly relates to a method that makes it possible to detect specific defects more reliably, and a detection system and a detection program for implementing the method.

RELATED ART

In terms of enhancing yield and reliability in production processes of semiconductor devices, inspection techniques for detecting defects on the surface of wafers to be substrates for semiconductor devices have become extremely more important. Inspection systems for detecting various kinds of defects on wafer surfaces include a system for inspecting a wafer surface using an optical technique to detect defects as light points corresponding to the positions of defects on the wafer surface.

Examples of such surface inspection systems include a surface inspection system using the principle of laser scattering. This laser scattering type surface inspection system irradiates a wafer surface with laser. When a defect is formed at the irradiated position, light is scattered from the wafer surface. The scattered light is detected by a photodetector such as a light receiving element or a photomultiplier tube, and is converted into an electrical signal by a photoelectric conversion element. Thus, the defect is detected as a light point. The wafer is disposed on a stage, and the entire surface of the wafer surface is scanned with laser by moving the wafer in the radial direction of the wafer while the wafer is rotated. An encoder is attached to the stage, so that detected light points can be associated with the relevant positions in the wafer surface. Thus, a "light point map" can be obtained, which is an in-plane position data of the light points.

Here, in this description, in a case where a wafer surface is inspected by an optical technique, defects, flaws, foreign matters, etc. on the wafer surface which can be detected as light points are collectively referred to as "defects". Such defects mainly include grow-in defects such as COPs (Crystal Originated Particles), FPDs (Flow Pattern Defects), and LSTDs (Laser Scattering Tomography Defects), which are introduced to a crystal used for forming a wafer in a process step of pulling the crystal. Such defects further include defects (such as flaws or scratches) formed on the wafer surface due to processing after a slicing process. Furthermore, such defects may include foreign matters left on the wafer surface (such as impurities, particles, and polishing agent residue).

Here, most of light points are simply points or short lines in a light point map irrespective of the kind of defects resulting in the light points; therefore, it is difficult to determine what kind of defects have caused each of the light points. As a matter of fact, defects shown as light points in the above laser scattering type surface inspection system, for example, are collectively referred to as LPDs (Light Point Defects) irrespective of their kinds.

There are some defects acceptable (not causing trouble) in products or defects of which occurrence is expected from the beginning; however, there are also defects which adversely affect the device characteristics, device production yield or reliability. For example, in a case of inspecting a surface of a wafer not in a device production process but in a wafer production process, many COPs are detected as light points in a light point map of the wafer into which COPs which would form a gettering sink are positively introduced, which does not cause any wafer quality problem. On the other hand, when the surface of this wafer is partially scratched, devices cannot be fabricated on the scratched portion, which consequently reduces the device production yield and ruins the reliability of the whole wafer. Therefore, techniques for determining whether or not light points resulted from such undesired defects are present in a light point map have been desired.

CN 1822343 (A) discloses a defect detection system. Using the defect detection system, a light point density range of a specified region on a wafer surface is previously set, and when the light point density of the specified region in a light point map obtained by inspecting the wafer with the surface inspection system exceeds the above set range, defects are determined to be present.

RELATED ART DOCUMENTS

Patent Document

Patent Document 1: CN 1822343 (A)

DISCLOSURE OF THE INVENTION

Problems to be Solved by the Invention

The present inventor studied in detail how defects which adversely affect wafer manufacturing are shown in a light point map, and what causes the defects adversely affecting the wafer manufacturing. Then, although the details will be described later, he found the fact that defects which occur due to specific causes include defects which are not formed without the relevant cause and characteristically occur in a substantially fixed position on a wafer surface when the cause occurs. Accordingly, defects which occur due to specific causes and which are known to occur in specific portions on a wafer surface depending on the causes are herein referred to as "specific defects" in this description.

When specific defects are present, there are light points resulted from the relevant specific defects on a light point map. However, the light points in the light point map also include light points resulted from defects other than the specific defects, namely, defects which randomly occur with the defect positions not being limited to specific positions or ranges (hereinafter referred to as "non-specific defects" in this description) such as the above-described COPs. Both of such defects are generally mixed in the light point map. Therefore, it is required to appropriately determine whether or not there are light points resulted from specific defects in a light point map, in other words, whether or not specific defects have occurred.

Here, those skilled in visual observation, who are proficient in fully associating a plurality of kinds of specific defects with respective positions in a wafer surface where the specific defects would occur, can probably determine whether or not specific defects have occurred by means of sensory evaluation by visually observing the light point map. However, in the sensory evaluation by visual observation, the determination of whether or not specific defects have occurred depends on the skill level of the inspector. Besides, the determination by visual observation is not favorable because it is difficult in cases where the density of non-specific defects is high.

Further, a method of setting a threshold value of the light point density with respect to a region where specific defects are expected to occur in a light point map and determining that specific defects have occurred when the light point density measured in the region exceeds the threshold value as in CN 1822343 (A) is conceivable. However, whether or not specific defects have occurred cannot be reliably determined in some cases due to the relationship between the number of light points resulted from non-specific defects in the region and the threshold level set, which is a problem. For example, when many light points resulted from COPs which are non-specific defects are present on the entire wafer surface, the specific defects would be determined to have occurred if the light point density in the region subjected to the determination (determination region) exceeds the threshold value due to the light points resulted from COPs although specific defects have not actually occurred. On the other hand, when there are few light points resulted from COPs in the entire wafer surface, the light point density in the determination region does not exceed the threshold value. Accordingly, the region would be determined to have no specific defects although specific defects have actually occurred.

In view of the above problems, an object of the present invention is to provide a detection method, a detection system, and a detection program which allow specific defects that would occur on a wafer surface to be detected more reliably.

Means for Solving the Problem

As the present inventor have made various studies to achieve the above object, he found that specific defects can be detected more reliably by effectively perceiving the contrast between light points originated from specific defects and its surroundings, not by setting a threshold value of the light point density with respect to the region where specific defects are expected to occur, and thus he completed the present invention. The present invention is based on the above knowledge and studies, and it primarily includes the following components.

A method of detecting a specific defect of the present invention includes the steps of:

acquiring a light point map which is in-plane position information of a light point detected in a position corresponding to a defect on a surface of a wafer by irradiating the surface of the wafer with light;

specifying a determination region where a specific defect is expected to be formed and a reference region which is a given region other than the determination region in the light point map, and calculating a ratio of a light point density of the determination region to a light point density of the reference region; and determining whether or not the specific defect is formed based on the calculated ratio. Note that the "light point density" herein means the number of light points per unit area.

Further, the determination step can determine that the specific defect is formed when the calculated ratio is equal to or higher than a predetermined threshold value.

Furthermore, in the acquisition step, light point maps of a plurality of wafers having the same shape may be acquired, and in the calculation step, the ratio can be calculated using an overlap light point map obtained by overlaying the light point maps of the plurality of wafers onto one another instead of using the light point map.

Alternatively, in the acquisition step, an overlap light point map obtained by overlaying light point maps of a plurality of wafers having the same shape onto one another may be acquired instead of the light point map, and in the calculation step, the ratio may be calculated using the overlap light point map instead of using the light point map.

Preferably, light point maps of a plurality of wafers having the same shape are acquired in the acquisition step, and before determining whether or not a plurality of kinds of specific defects are formed, the specific defects are previously classified as a first group of specific defects on which the calculation step is performed using the light point map of a given one of the plurality of wafers, and a second group of specific defects on which the calculation step is performed using an overlap light point map obtained by overlaying the light point maps of the plurality of wafers onto one another.

A system for detecting a specific defect in accordance with the present invention includes:

an acquisition unit for acquiring a light point map which is in-plane position information of a light point detected in a position corresponding to a defect on a surface of a wafer by irradiating the surface of the wafer with light;

a storage unit for storing data on a determination region where a specific defect is expected to be formed and a reference region which is a given region other than the determination region in the light point map;

a calculation unit for calculating a ratio of a light point density of the determination region to a light point density of the reference region in the light point map; and a determination unit for determining whether or not the specific defect is formed based on the calculated ratio.

Another method of detecting a specific defect according to the present invention includes the steps of:

detecting a defect on a surface of a wafer as a light point by irradiating the surface of the wafer with light;

creating a light point map which is in-plane position information of the detected light point;

specifying a determination region where a specific defect is expected to be formed and a reference region which is a given region other than the determination region in the light point map, and calculating a ratio of a light point density of the determination region to a light point density of the reference region; and determining whether or not the specific defect is formed based on the calculated ratio.

This method also further includes a step of creating an overlap light point map obtained by overlaying light point maps of a plurality of wafers having the same shape onto one another, and the ratio may be calculated in the calculation step using the overlap light point map instead of using the light point map.

Another system for detecting a specific defect in accordance with the present invention includes:

a detection unit for detecting a defect on a surface of a wafer as a light point by irradiating the surface of the wafer with light;

an analysis unit for creating a light point map which is in-plane position information of the light point on the surface of the wafer based on output from the detection unit;

a storage unit for storing data on a determination region where a specific defect is expected to be formed and a reference region which is a given region other than the determination region in the light point map;

a calculation unit for calculating a ratio of a light point density of the determination region to a light point density of the reference region in the light point map; and a determination unit for determining whether or not the specific defect is formed based on the calculated ratio.

A program of the present invention is a program allowing a computer to execute the steps of the above methods for detecting a specific defect.

Effect of the Invention

According to the present invention, the light point density ratio of a determination region to a reference region is calculated to determine whether or not specific defects have occurred based on the ratio. Therefore, regardless of the number of non-specific defects such as COPs which may randomly occur in the whole wafer, the contrast between light points resulted from specific defects and their surroundings can be effectively perceived. Consequently, specific defects can be detected more reliably.

BEST MODE FOR CARRYING OUT THE INVENTION

Figure 1:
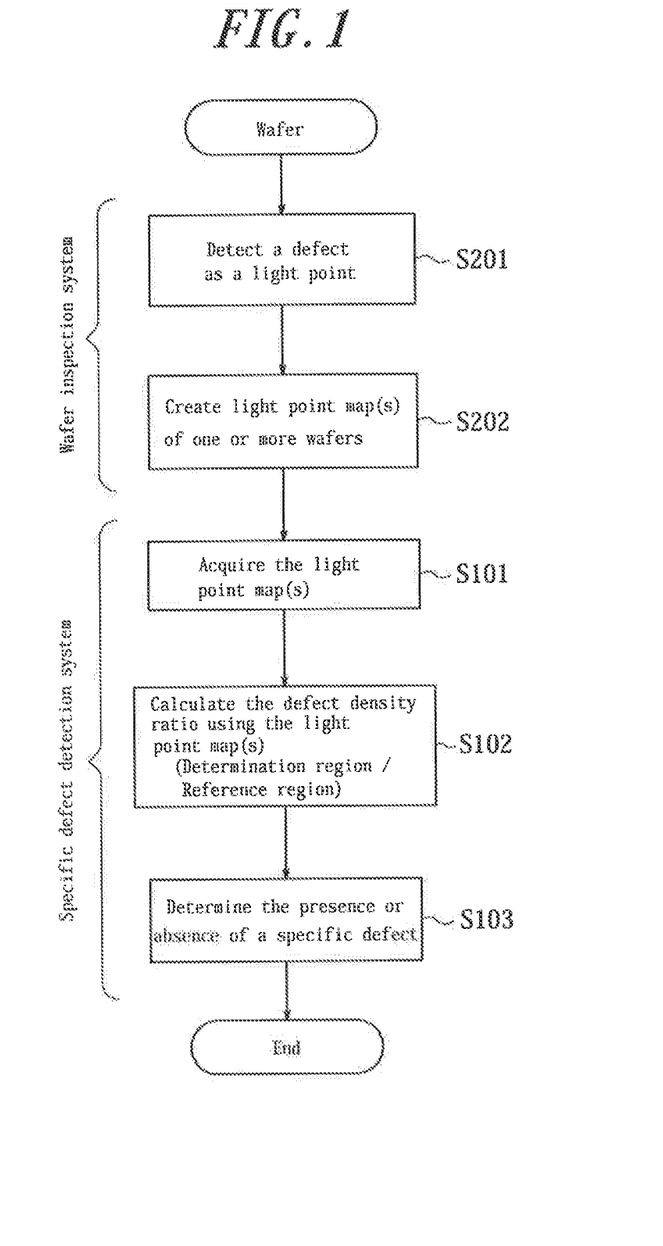
FIG. 1 is a flow chart of a representative method of detecting specific defects in accordance with the present invention.
Figure 2:
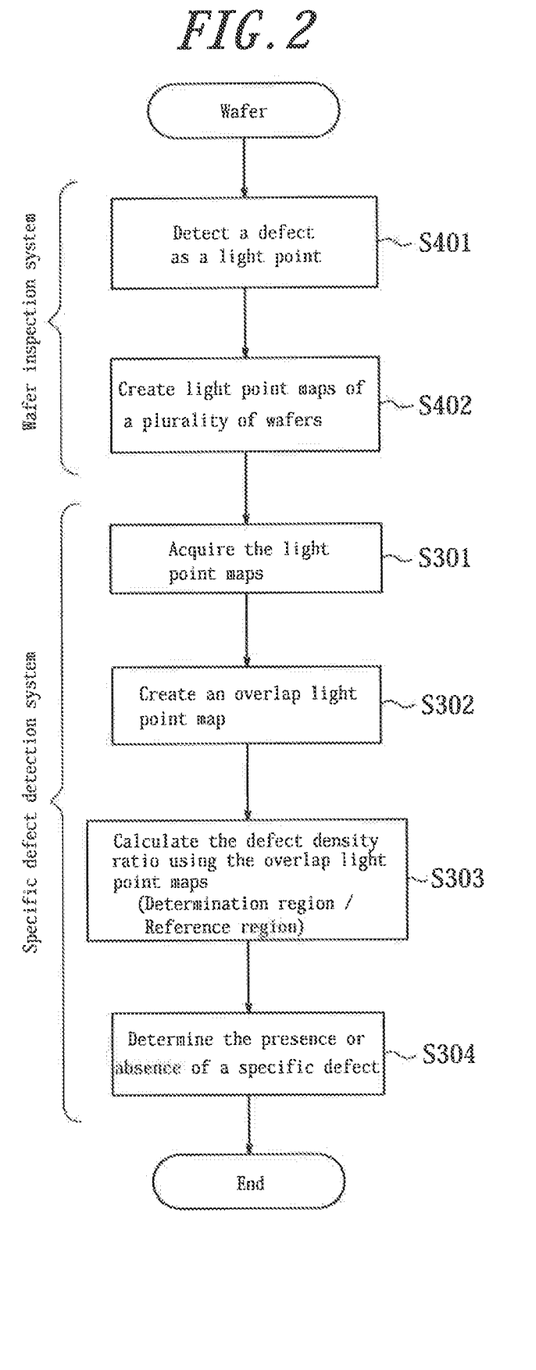
FIG. 2 is a flow chart of another method of detecting specific defects in accordance with the present invention.
Figure 3:
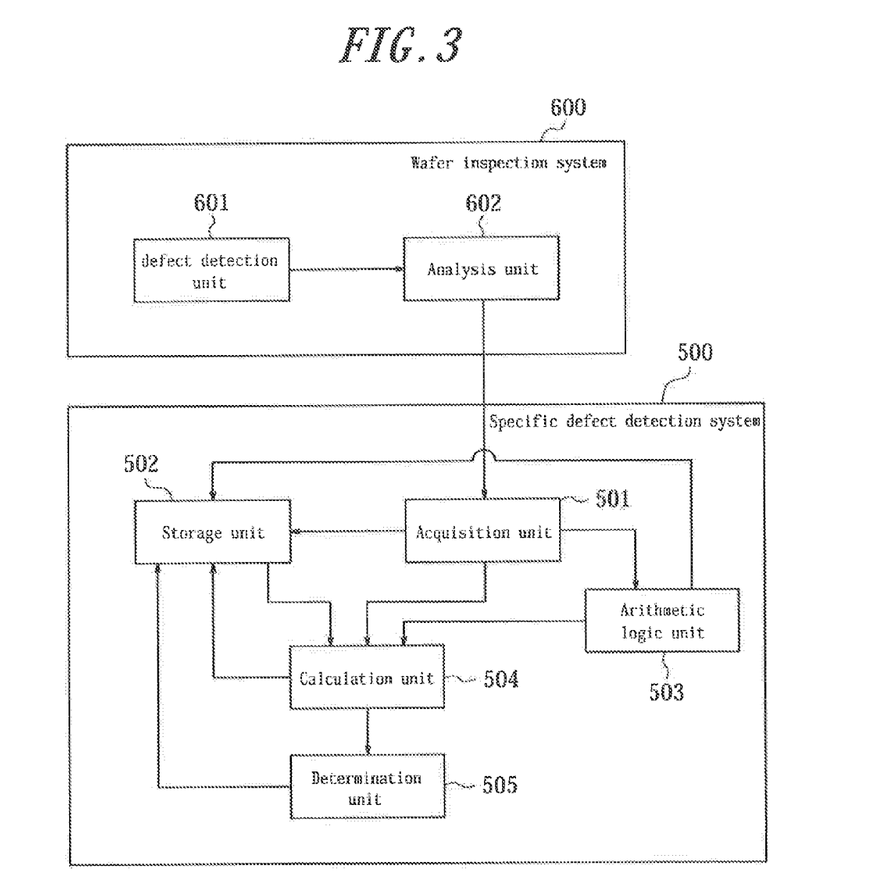
FIG. 3 is a block diagram of a representative system for detecting specific defects in accordance with the present invention.

Embodiments of the present invention will be described below with reference to the drawings to further demonstrate the subject matter of the present invention. FIG. 1 and FIG. 2 are flow charts of methods of detecting specific defects in accordance with embodiments of the present invention. FIG. 3 is a block diagram including a detection system for performing these detection methods.

Wafer Inspection System

First, a known wafer inspection system 600 such as a laser scattering type surface inspection system includes a defect detection unit 601 and an analysis unit 602.

The defect detection unit 601 is not limited in particular as long as it detects defects as light points on a surface of a wafer by irradiating the surface of the wafer with light. For example, as described above, the wafer surface is irradiated with laser, and light scattered from the wafer surface can be detected to detect defects as light points. Alternatively, the wafer surface may be irradiated with light, and regular reflection light from the wafer may be detected with an imaging device such as a CCD to process the difference of brightness between the pixels; thus, wafer defects and their in-plane distribution may be detected as light points.

Figure 4A:
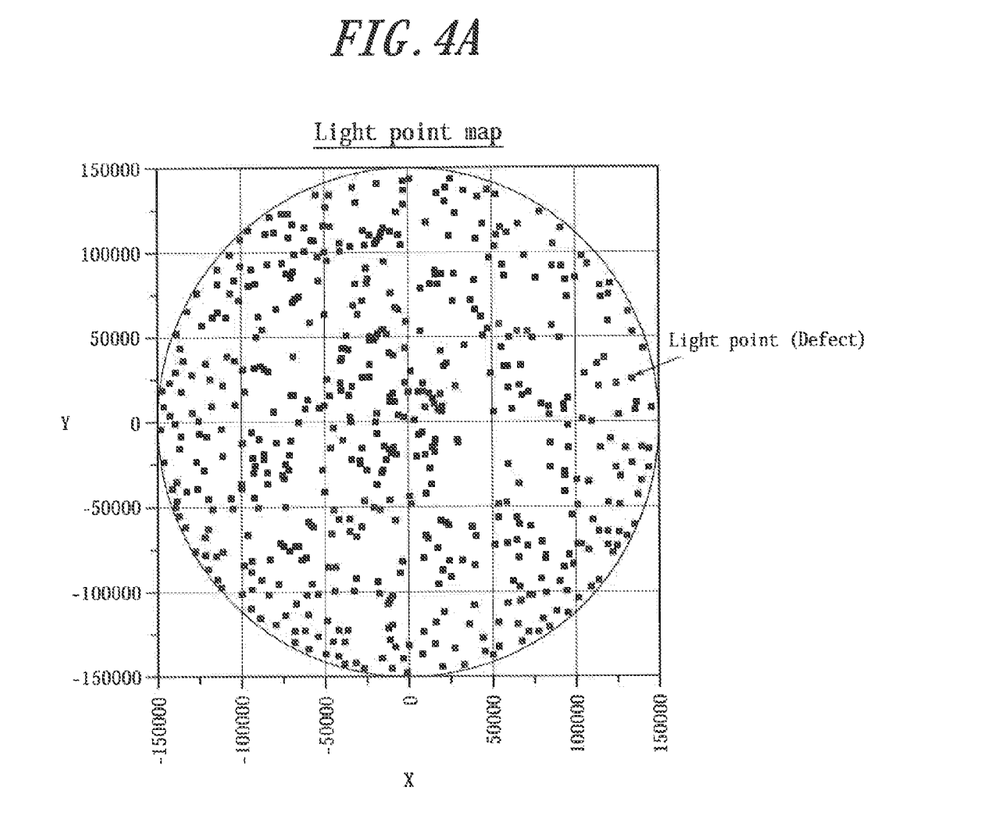
FIG. 4A shows an example of a light point map containing light points resulted from specific defects arranged in a ring shape at the center of a wafer surface.
Figure 4B:
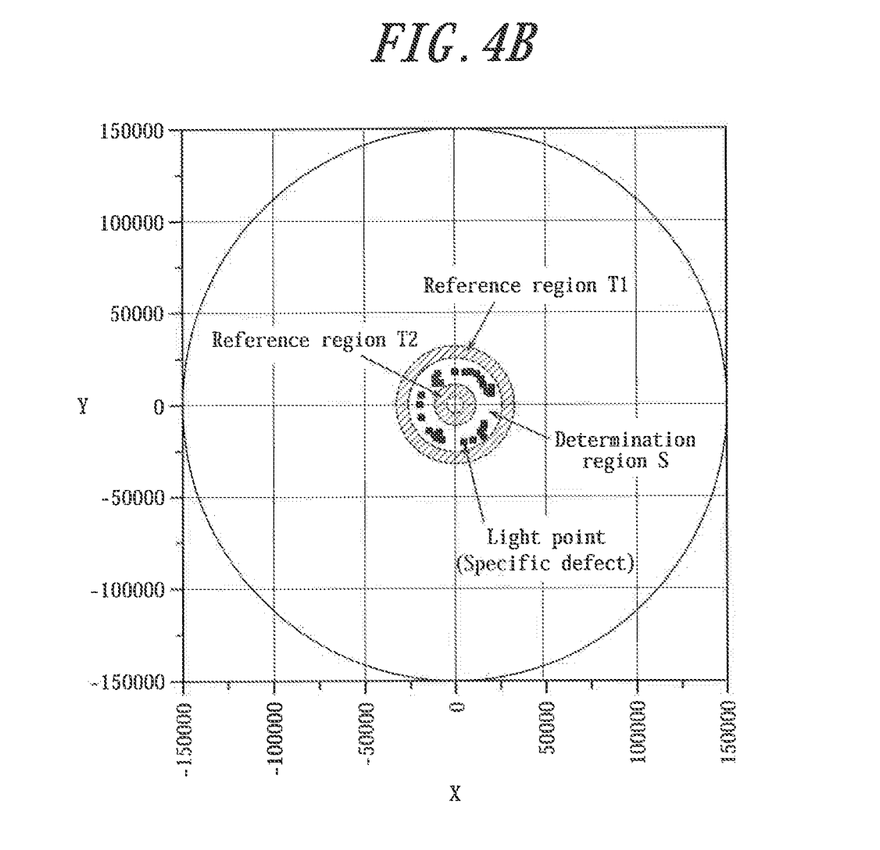
FIG. 4B is a light point map selectively showing only the light points resulted from the specific defects in FIG. 4A.
Figure 4C:
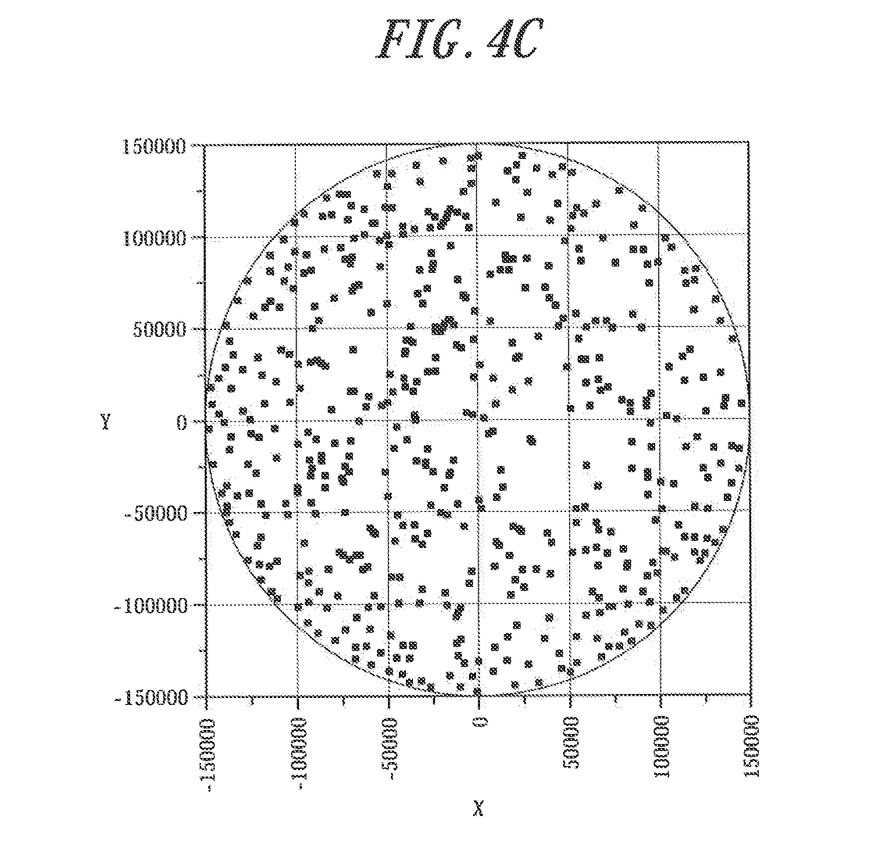
FIG. 4C is a light point map selectively showing the light points except for the ones resulted from the specific defects in FIG. 4A.

The analysis unit 602 creates, a light point map based on the detection data output from the detection unit 601. Here, a "light point map" in the specification means wafer in-plane position data of light points resulted from defects in a single wafer, detected by the defect detection unit 601. The "light point map" includes information of, for example, whether light points have occurred or not and the in-plane coordinate in paired texts data, and is not limited to the state where in-plane position data of light points are actually output to a display or the like as shown in FIGS. 4A to 4C. This wafer inspection system 600 can create a light point map after inspecting a single wafer, but normally inspects all the wafers in a batch of wafers manufactured in the same wafer production apparatus to create their respective light point maps.

Embodiment 1

System for Detecting Specific Defects

Next, a specific defect detection system 500 of this embodiment includes an acquisition unit 501, a storage unit 502, an arithmetic logic unit 503, a calculation unit 504, and a determination unit 505.

The acquisition unit 501 acquires a light point map of a single wafer or a plurality of wafers from the analysis unit 602 of the wafer inspection system 600. The acquired light point map is sent to the calculation unit 504, and is used for calculating the light point density ratio to be described later. Further, the acquired light point map may be stored in the storage unit 502. The acquisition unit 501 has a function of a control unit for controlling the acquisition of a light point map from the analysis unit 602, and can realize this function specifically with the use of a central processing unit (CPU) inside a computer.

The storage unit 502 can be realized using a hard disk, a ROM, or a RAM to store data on a determination region where specific defects are expected to occur and a reference region which is a given region other than the determination region in the light point map. The storage unit 502 stores for example, data on the causes of defect formation, position data of a region where specific defects are expected to occur due to the causes (that is, the foregoing determination region in the light point map, where light points resulted from the specific defects are expected to be formed), and position data on the reference region in the light point map as one set about each of the kinds of the specific defects.

The calculation unit 504 receives data of light point maps from the acquisition unit 501 or the storage unit 502, and further receives data on the determination region and the reference region in association with the kinds of the specific defects from the storage unit 502. Subsequently, the ratio of the light point density of the determination region to the light point density of the reference region in the light point map is calculated. The calculation result may be stored in the storage unit 502.

The determination unit 505 determines whether or not specific defects have occurred based on the ratio calculated by the calculation unit 504. The determination result may be stored in the storage unit 502.

When the acquisition unit 501 acquires light point maps of a plurality of wafers having the same shape, the arithmetic logic unit 503 overlays the light point maps of the plurality of wafers onto one another with the in-plane coordinates of the plurality of wafers aligned with each other to create an "overlap light point map". The wafers are generally provided with a cut-out referred to as a notch or an orientation flat for the purpose of aligning the orientation of the wafers in a wafer production process. The light point maps can be overlaid onto one another such that the positions of the wafer centers and the positions of the cut-outs of the wafers are respectively aligned. The created overlap light point map may be stored in the storage unit 502. Further, when the light point density ratio (determination region/reference region) is calculated using the overlap light point map as will be described later, the data of the overlap light point map is sent to the calculation unit 504. Note that the overlap light point map is not limited to the state where a plurality of light point maps overlapping one another are actually shown on a display or the like as shown in FIG. 6, and includes digital data of the in-plane position data of light points, as the light point maps do.

The arithmetic logic unit 503, the calculation unit 504, and the determination unit 505 all perform data processing in the specific defect detection system, and the data processing can be realized by a central processing unit (CPU) in the computer. Note that the arithmetic logic unit which creates the overlap light point map is not necessary in this embodiment. For example, the overlap light point map may be created in the wafer inspection system 600, and the overlap light point map may be acquired by the acquisition unit 501 of the system in this embodiment.

The light point density ratio may be calculated by the calculation unit 504 with respect to the overlap light point map instead of the light point maps, which will be discussed in greater detail. In this case, the calculation unit 504 receives data on an overlap light point map from, the arithmetic logic unit 503 or the storage unit 502, and further receives data on the determination region and the reference region in association with the kinds of the specific defects from the storage unit 502. Subsequently, the calculation unit 504 calculates the ratio of the light point density of the determination region to the light point density of the reference region in the overlap light point map. The calculation result may be stored in the storage unit 502. Note that when the overlap light point map is created in the wafer inspection system 600 and the overlap light point map is acquired by the acquisition unit 501, the calculation unit 504 receives the data of the overlap light point map from the acquisition unit 501.

Embodiment 2

First Method of Detecting Specific Defects

Next, a wafer inspection process and a method of subsequent detection of specific defects in accordance with this embodiment will be described with concrete examples. The defect detection unit 601 of the wafer inspection system 600 irradiates a surface of a wafer with light and detects defects on the surface of the wafer as light points (step S201). Subsequently, the analysis unit 602 creates a light point map which is the in-plane position data of the detected light points (step S202). In this wafer inspection process, a single wafer or a plurality of wafers are subjected to the above process steps.

A method of detecting specific defects following the above process in accordance with this embodiment will be described. The acquisition unit 501 acquires a light point map of a single wafer or a plurality of wafers (step S101). Here, an example of a light point map is shown. First, a polished wafer was produced by a known method. Specifically, a silicon crystal pulling process is performed using the CZ method (Czochralski method), and then working processes such as slicing, rough grinding (lapping), etching, polishing, and cleaning were performed to obtain a polished wafer. A given batch was extracted from a large number of wafers manufactured by a plurality of manufacturing apparatuses, and the light point map obtained by performing surface inspection on one of the batch of wafers is shown in FIG. 4A. In this light point map, an aggregation of a plurality of light points arranged in a ring shape was observed at the center region. This ring-shaped light point group is constituted by light points resulted from flaws caused by maladjustment of a wafer adsorption jig in a suction pad shape. Since the adsorption jig attached to a robot hand has a circular shape, the light points formed on a wafer surface due to this cause are found to always draw a circular pattern with substantially same radii centered on the wafer center. On the other hand, wafers produced by a manufacturing apparatus without this cause did not have such a ring-shaped light point group. Therefore, defects causing such a ring-shaped light point group were recognized as "specific defects".

Next, in a light point map, a determination region where specific defects are expected to occur and a reference region which is a given region other than the determination region are specified. The calculation unit 504 calculates the ratio of the light point density of the determination region to the light point density of the reference region (step S102). Subsequently, a detailed description will be made with reference to FIGS. 4A to 4C. FIG. 4B is a light point map of the extracted light points caused by the ring-shaped specific defects. A region including such a position where specific defects are expected to occur is specified as a determination region S corresponding to the specific defects. Note that regions where other specific defects due to other causes would occur are known; therefore, the region explained earlier is defined as a determination region.

Then, a given region other than the determination region is defined as a reference region. In the example of FIGS. 4A to 4C, as shown in FIG. 4B, ring-shaped reference regions T1 and T2 with a predetermined width were provided inside and outside the ring-shaped determination region S, respectively. Note that FIG. 4C shows a light point map of the light points except for the ones caused by the specific defects.

Figure 5:
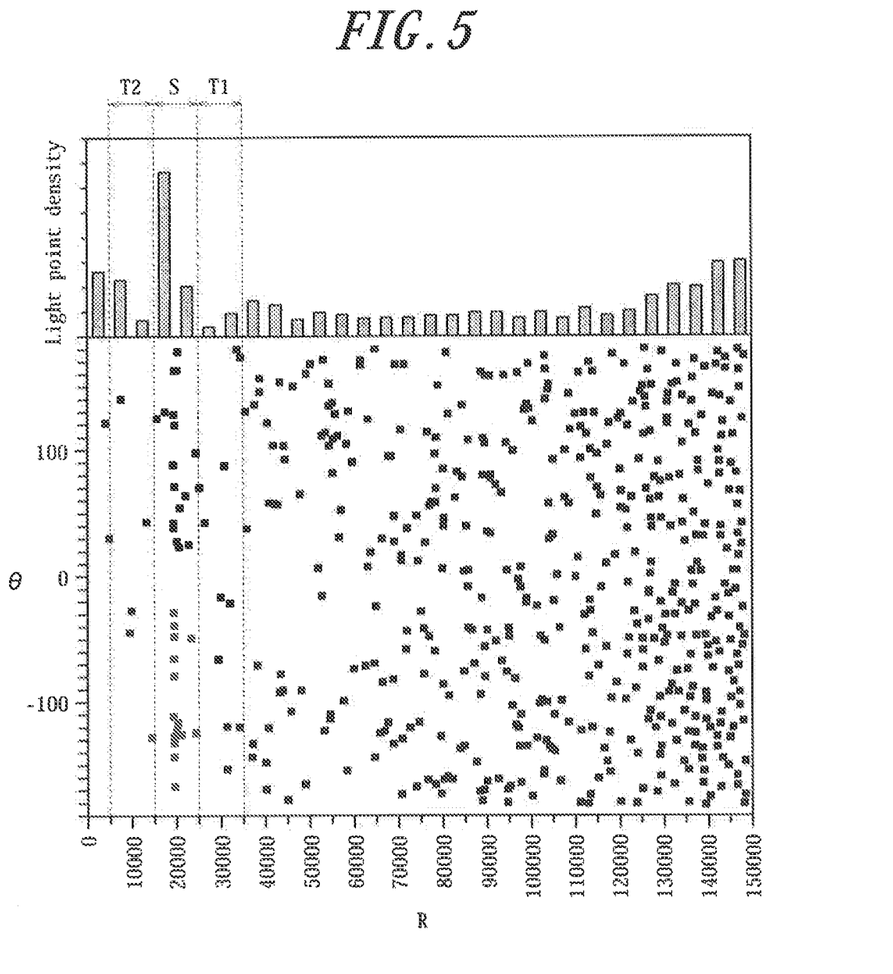
FIG. 5 is a graph of plots of the light point map in FIG. 4A on R-θ coordinate in which the distance R from the wafer center is represented by the horizontal axis, and the angle θ formed between the X-axis (X≥0) and the straight line from each of spots to the origin of the X-Y coordinate is represented by the vertical axis. The bars on the R-axis each represent the light point density of the ring shaped region having a predetermined width at regular intervals from the wafer center.

In the example of FIGS. 4A to 4C, both the determination region and the reference regions are ring-shaped regions having a center at the wafer center. Correspondingly, as shown in FIG. 5, the light point map of FIG. 4A is replotted on R-θ coordinate in which the distance R from the wafer center is represented by the horizontal axis, and the angle θ formed between the X-axis (X≥0) and the straight line from each of spots to the origin of the X-Y coordinate is represented by the vertical axis. In this R-θ coordinate, the determination region S and the reference regions T1 and T2 are shown by broken lines. Here, in the example of FIGS. 4A to 4C in which specific defects are formed, in addition to light points caused by non-specific defects such as COPs, light points caused by specific defects are concentrated at the determination region S, which results in higher light point density of the determination region S than that of the reference regions T1 and T2 where only light points caused by non-specific defects are present. The light point density ratio (the determination region S/the reference regions T1+T2) in this embodiment has a value of 3.3, which shows an obviously significant difference. Consequently, the value of the light point density ratio (determination region S/reference regions T1+T2) provides an indication of whether or not specific defects have occurred.

Finally, the determination unit 505 determines whether or not specific defects have occurred based on the calculated light point density ratio (step S103).

If the number of light points or the light point density in the determination region S is used as an indication, whether or not specific defects have occurred would not be accurately determined depending on the number of non-specific defects as described above. However, the light point density ratio is an indication which is easily influenced by the presence or absence of light points resulted from specific defects, namely, an indication which minimizes the effect of light points resulted from non-specific defects. Therefore, specific defects can be detected more reliably by the method of this embodiment. When specific defects are determined to have occurred, the following measures can be taken: eliminating the cause, eliminating specific defects on the wafer in some cases, or the like. In the example of FIGS. 4A to 4C, a measure of replacing or repairing the adsorption jig applied to the wafer can be taken.

Here, in the determination step (S103), specific defects can be determined to have occurred when the calculated value of the light point density ratio is equal to or higher than a predetermined threshold value. The manner of setting the threshold value is not limited in particular, but the threshold value can be set as follows.

First, a significance test is performed with respect to the light point density of a determination region R and the light point density of a reference region. As a result, the minimum light point density ratio determined to cause significant difference can be defined as a threshold value. Specifically, the chi-square ($\Psi^2$) test is performed to determine whether or not the densities of the determination region and the reference region have significant difference.

Further, considering non-uniformity in the in-plane distribution of light points caused by non-specific defects, it was found that the threshold value of the significant light point density ratio (determination region/reference region) is preferably set in the range of 1.05 to 50. When the threshold value is set less than 1.05, specific defects would be determined to be present due to non-uniformity in the in-plane distribution of light points caused by non-specific defects even when there are no specific defects. On the other hand, when the threshold value is set more than 50, the threshold value is too high, so that specific defects would be determined to be absent even when specific defects are present.

In this embodiment, the position of the reference region with respect to that of a given determination region is not limited in particular as long as it is a region other than the determination region. For example, as shown in FIG. 4B, the reference region may be provided in a region adjacent to the determination region. Alternatively, the entire wafer surface other than the determination region may be defined as a reference region. In this case, even if non-uniformity in the in-plane distribution of non-specific defects is accidentally high, whether or not specific defects have occurred can be determined reliably. In addition, when plurality kinds of specific defects are expected to occur, a reference region is preferably provided in an area except for the determination regions corresponding to those specific defects. This is because a reference region corresponding to a given determination region does not overlap with another determination region, so that accurate determination would not be disrupted.

Embodiment 3

Second Method of Detecting Specific Defects

Next, a wafer inspection process and a method of subsequent detection of specific defects in accordance with another embodiment will be described with reference to FIG. 2. The defect detection unit 601 of the wafer inspection system 600 irradiates a surface of a wafer with light and detects defects on the surface of the wafer as light points (step S401). Subsequently, the analysis unit 602 creates a light point map (step S402). In the wafer inspection process of this embodiment, a plurality of wafers having the same shape (for example, of a batch) are subjected to the above process steps.

In this embodiment, the acquisition unit 501 acquires light point maps of the above plurality of wafers (step S301). Then, the arithmetic logic unit 503 overlays the light point maps of these plurality of wafers onto one another with the in-plane coordinates of the wafers aligned with each other to create an overlap light point map (step S302). In this embodiment, the calculation unit 504 calculates the defect density ratio (determination region/reference region) using this overlap light point map instead of the light point maps (step S303), and the determination unit 505 determines whether or not specific defects have occurred based on the calculated light point density ratio (step S304).

Figure 6A:
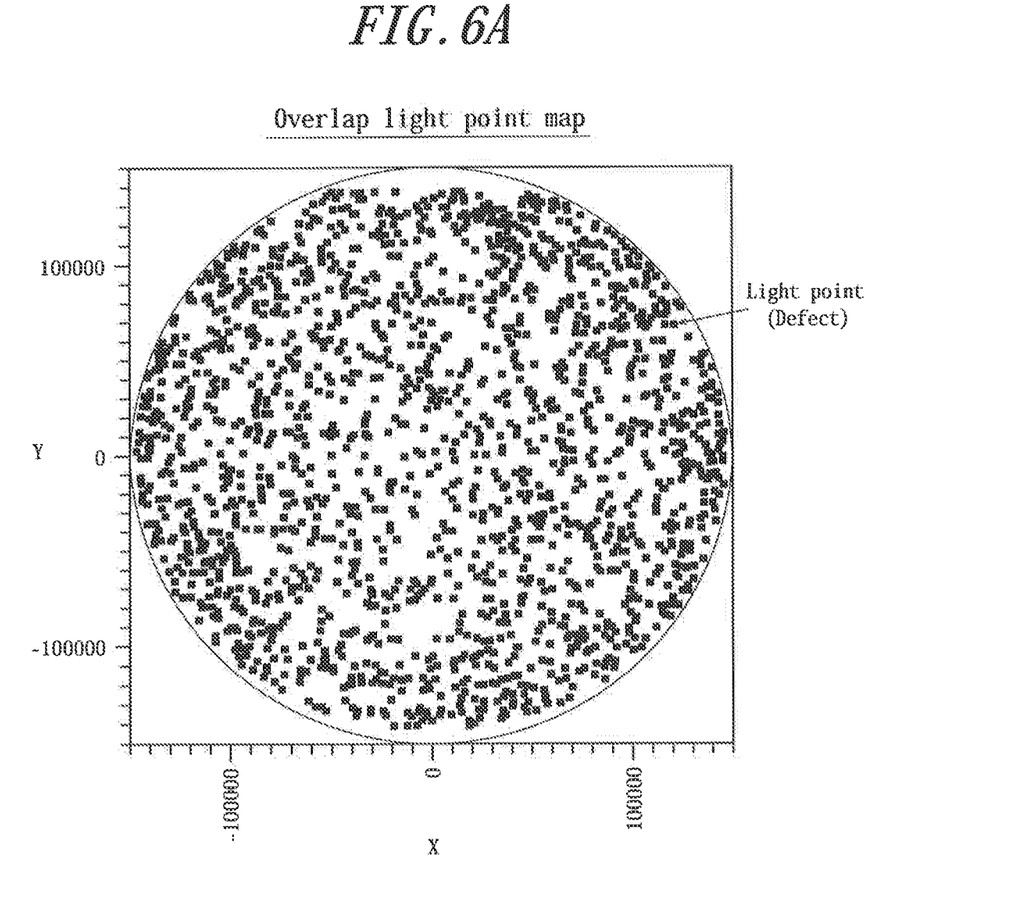
FIG. 6A shows an example of an overlap light point map containing light points resulted from specific defects arranged in a ring shape near the end portion of a wafer surface.

Here, an example of an overlap light point map is shown. First, a polished wafer was produced by a similar method to FIGS. 4A to 4C. Then, a batch (120 sheets) of wafers treated by a chemical treatment system different from the chemical treatment system used in the wafer manufacturing process (etching process) in FIGS. 4A to 4C were subjected to surface inspection to create light point maps. An overlap light point map obtained after that by overlaying the light point maps of the batch of wafers onto one another is shown in FIG. 6A. It is difficult to examine this overlap light point map by visual observation; however, there is an aggregation of a plurality of light points arranged in a ring shape at an end portion of the wafer surface due to a specific cause, and an overlap light point map of extracted spots of these is shown in FIG. 6B.

This ring-shaped light point group is resulted from flaws on each wafer made in the chemical treatment step after the slicing step. The chemical treatment system performs chemical treatment of the wafer surface while rotating the wafer. On this occasion, in some chemical treatment systems, a robot moving above the wafer would damage a part of the wafer surface at a certain distance from the wafer center immediately before stopping the rotation. The timing of operation of the robot is not synchronized with the rotation of the wafer; therefore, a batch of the plurality of wafers each has only a point of flaw at a certain distance from the center. However, when the wafers are overlaid onto one another, the flaws made due to this cause are distributed substantially in a circular shape with radii of a certain distance from the wafer center. Thus, although each wafer has only one light point on the light point map resulted from this kind of defect, the light points constitute a circular shape with substantially the equal radii centered on the wafer center on the created overlap light point map. Meanwhile, wafers subjected to other chemical treatment systems in the wafer manufacturing process did not have such defects. In view of the foregoing, defects causing such a ring-shaped light point group were recognized as "specific defects".

Figure 6B:
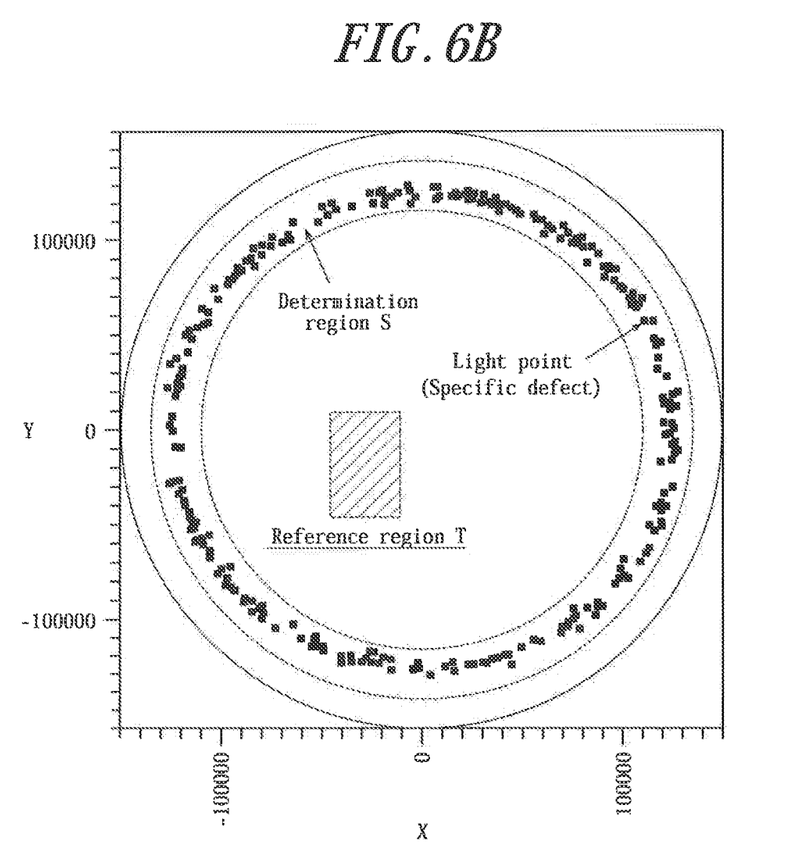
FIG. 6B is an overlap light point map selectively showing only the light points resulted from the specific defects in FIG. 6A.

Next, a determination region S was provided as shown in FIG. 6B as a region where specific defects are expected to be formed on the overlap light point map. Further, a reference region T was provided in a region other than the determination region. In this embodiment, the reference region T was provided as a rectangular region having a given size at a position other than the determination region S. Note that FIG. 6C shows a light point map of the light points except for the ones caused by the specific defects.

Figure 6C:
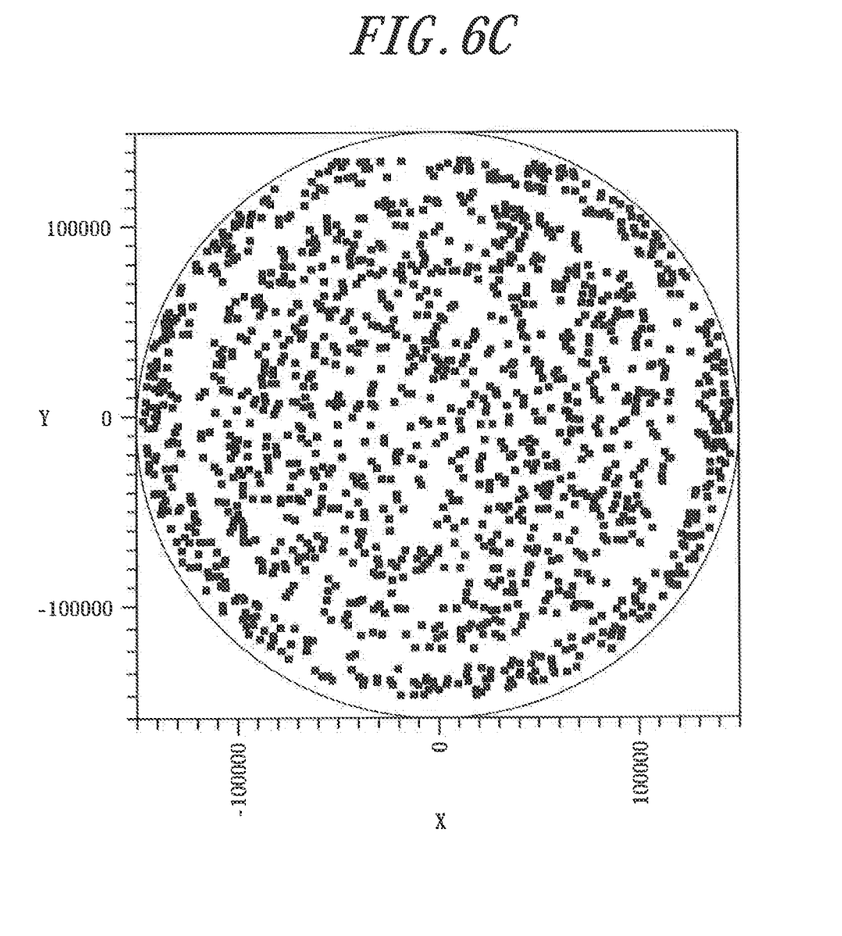
FIG. 6C is an overlap light point map selectively showing the light points except for the ones resulted from the specific defects in FIG. 6A.
Figure 7:
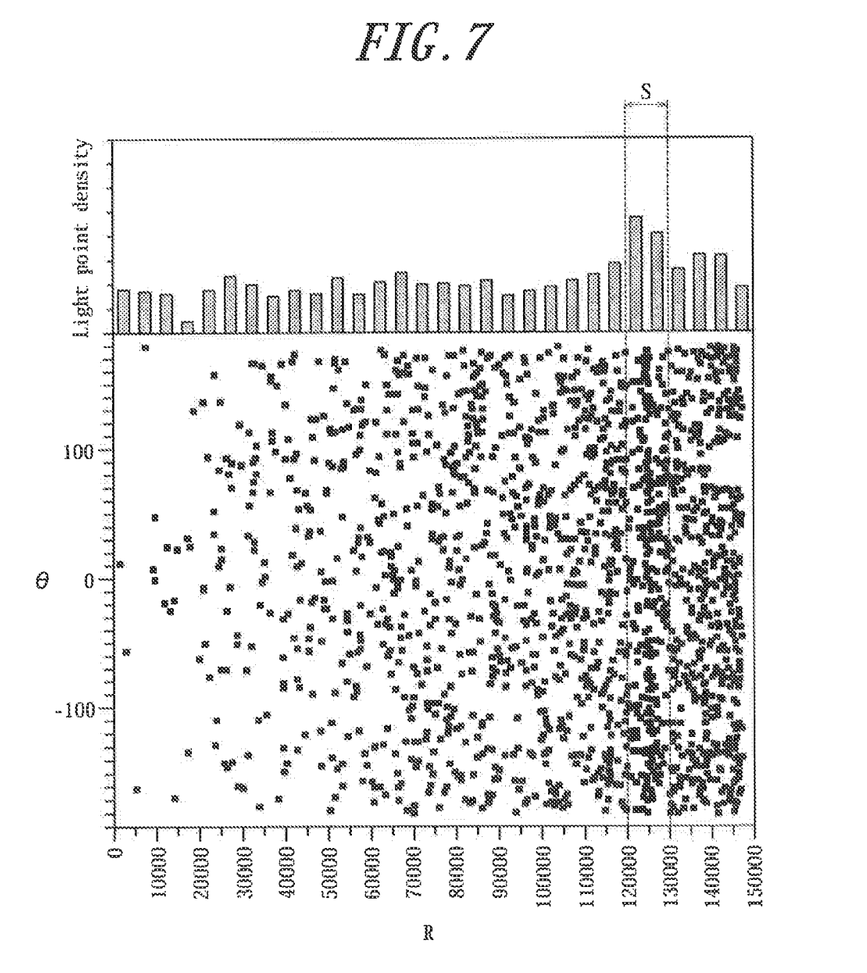
FIG. 7 is a graph of plots of the overlap light point map in FIG. 6A on R-θ coordinate in which the distance R from the wafer center is represented by the horizontal axis, and the angle θ formed between X-axis (X≥0) and the straight line from each of spots to the origin of the X-Y coordinate is represented by the vertical axis. The bars on the R-axis each represent the light point density of the ring shaped region having a predetermined width at regular intervals from the wafer center.

FIG. 7 shows a graph of the overlap light point map in FIG. 6 plotted on R-θ coordinate. The determination region S is shown by broken lines. Here, in this example in which specific defects are formed, in addition to light points caused by non-specific defects such as COPs, light points caused by specific defects are concentrated at the determination region S, which results in higher light point density of the determination region S than that of the reference region T where only light points caused by non-specific defects are present. The light point density ratio (the determination region S/the reference region T) in this embodiment has a value of 1.05, which shows an obviously significant difference. Consequently, the value of the light point density ratio (determination region S/reference region T) provides an indication of whether or not specific defects have occurred, also in the overlap light point map. Thus, when specific defects are determined to be present, the following measures can be taken: eliminating the cause, eliminating specific defects on the wafer in some cases, or the like. In the example of FIG. 6A to 6C, the robot of the chemical treatment system used for manufacturing the batch of wafers can be adjusted so as not to damage the wafers.

As in this embodiment, in cases where a determination region corresponding to light points resulted from specific defects can be defined only after creating an overlap light point map, the light point density ratio is calculated using the overlap light point map. Thus, the specific defects can be detected more reliably. Other details are similar to those of the first specific defect detection method.

As described above, whether a light point map is used or an overlap light point map is used for calculating the light point density ratio depends on the kinds of the specific defects. Specifically, a light point map may be used when specific defects are such that a light point map of one given wafer has many light points resulted from the specific defects and a determination region can be defined on the light point map (hereinafter referred to as "first group of specific defects"). Otherwise, an overlap light point map is used when specific defects are such that a light point map has only one or a few light points resulted from the specific defects while an overlap light point map has many of them, and a determination region can be defined on the overlap light point map (hereinafter referred to as "second group of specific defects"). In the present invention, it is preferable that the first and second groups of specific defects are previously classified. Accordingly, the storage unit 502 stores data on which of the first and second groups the specific defects each belong to. Regarding the second group of specific defect, the storage unit 502 stores the position data of the determination region and the reference region defined on the overlap light point map.

Embodiment 4

Third Method of Detecting Specific Defects

In Embodiment 3, an overlap light point map is created in S302 of FIG. 2. In this embodiment, however, an overlap light point map is created in a wafer inspection system after S402. After that, a specific defect detection system acquires an overlap light point map instead of a light point map acquired in S301. Subsequently, in a calculation step, the defect density ratio is calculated using the overlap light point map instead of the light point map. Such a method also allows specific defects to be detected with accuracy.

Embodiment 5

Specific Defect Detection Method and Detection System

Examples of using the specific defect detection system 500 separate from the wafer inspection system 600 have been described so far; however, the specific defect detection system may be one system including a wafer inspection system. In this case, the acquisition unit 501 in FIG. 3 is not required, and the specific defect detection system is configured to include the defect detection unit 601, the analysis unit 602, the storage unit 502, the calculation unit 504, and the determination unit 505. Preferably, the specific defect detection system further includes the arithmetic logic unit 503. In this case, the light point map created by the analysis unit 602 is sent to the calculation unit 504, the storage unit 502, or the arithmetic logic unit 503. If the analysis unit 602 creates an overlap light point map as well, the arithmetic logic unit 503 is rendered unnecessary.

The steps of this detection method may include, except for step S101 in FIG. 1, detecting a defect on a surface of a wafer as a light point by irradiating the surface of the wafer with light (step S201); creating a light point map which is in-plane position information of the detected light point (step S202); specifying a determination region where a specific defect is expected to be formed and a reference region which is a given region other than the determination region in the light point map, and calculating a ratio of a light point density of the determination region to a light point density of the reference region (step S102); and determining whether or not the specific defect is formed based on the calculated ratio (step S103). Alternatively, the steps may include, except for the step S301 in FIG. 2, after the defect detection step (S401) and the light point map creation step (S402), creating an overlap light point map (step S302) and calculating the defect density ratio using the overlap light point map (step S303), thereby determining whether or not specific defects have occurred (step S304).

Specific Defects

Specific defects may include the specific defects mentioned in the description of the first and second specific defect detection methods. Other specific defects which allow a determination region to be defined on a light point map may include, for example, flaws formed in a given region of an end portion of the wafer when an edge clamp of a wafer transfer apparatus is damaged after the slicing step. However, the present invention is not limited to these specific defects. The present invention can be applied to any defects formed in the above known specific positions on wafer surfaces due to specific causes.

Program

An object of the present invention can be achieved by providing a system or an apparatus with a storage medium storing program codes of software realizing the processes of the above described embodiments and by reading and executing the program codes stored in the storage medium using a computer (or CPU or MPU) of the system or the apparatus. In this case, the program codes read from the storage medium realize the functions described in the above embodiments, and the program and the storage medium storing the program comprise the present invention.

Examples of the storage medium storing the program codes here may include flexible disks, hard disks, ROMs, RAMs, magnetic tapes, non-volatile memory cards, CD-ROMs, CD-Rs, DVDs, optical disks, magneto-optic disks, and MOs. Further, computer networks such as LAN (local area network) or WAN (wide area network) can be used for loading the program codes.

Thus, the present invention has been described to show examples of representative embodiments. However, the present invention is not limited to these embodiments, and various modifications can be made within the scope of the present invention.

INDUSTRIAL APPLICABILITY

According to the present invention, the light point density ratio of a determination region to a reference region is calculated, and whether or not specific defects have occurred is determined based on the ratio, which makes it possible to detect specific defects more reliably.

EXPLANATION OF REFERENCE NUMERALS

500: specific defect detection system
501: acquisition unit
502: storage unit
503: arithmetic logic unit
504: calculation unit
505: determination unit
S: determination region
T: reference region

What is claimed is:

1. A method of detecting a specific defect, comprising the steps of:
    acquiring a light point map which is in-plane position information of a light point detected in a position corresponding to a defect on a surface of a wafer by irradiating the surface of the wafer with light;
    specifying a determination region where a specific defect is expected to be formed and a reference region which is a given region other than the determination region in the light point map, and calculating a ratio of a light point density of the determination region to a light point density of the reference region; and
    determining whether or not the specific defect is formed based on the calculated ratio.

2. The method of detecting a specific defect according to claim 1, wherein the determination step determines that the specific defect is formed when the calculated ratio is equal to or higher than a predetermined threshold value.

3. The method of detecting a specific defect according to claim 1 or claim 2, wherein
    light point maps of a plurality of wafers having the same shape are acquired in the acquisition step, and
    the ratio is calculated in the calculation step using an overlap light point map obtained by overlaying the light point maps of the plurality of wafers onto one another instead of using the light point map.

4. The method of detecting a specific defect according to claim 1 or claim 2, wherein an overlap light point map obtained by overlaying light point maps of a plurality of wafers having the same shape onto one another is acquired in the acquisition step instead of the light point map,
    the ratio is calculated in the calculation step using the overlap light point map instead of using the light point map.

5. The method of detecting a specific defect according to claim 1 or claim 2, wherein
    light point maps of a plurality of wafers having the same shape are acquired in the acquisition step, and
    before determining whether or not a plurality of kinds of specific defects are formed, the specific defects are previously classified as a first group of specific defects on which the calculation step is performed using the light point map of a given one of the plurality of wafers, and a second group of specific defects on which the calculation step is performed using an overlap light point map obtained by overlaying the light point maps of the plurality of wafers onto one another.

6. A system for detecting a specific defect, comprising:
    an acquisition unit for acquiring a light point map which is in-plane position information of a light point detected in a position corresponding to a defect on a surface of a wafer by irradiating the surface of the wafer with light;
    a storage unit for storing data on a determination region where a specific defect is expected to be formed and a reference region which is a given region other than the determination region in the light point map;
    a calculation unit for calculating a ratio of a light point density of the determination region to a light point density of the reference region in the light point map; and
    a determination unit for determining whether or not the specific defect is formed based on the calculated ratio.

7. A method of detecting a specific defect, comprising the steps of:
    detecting a defect on a surface of a wafer as a light point by irradiating the surface of the wafer with light;
    creating a light point map which is in-plane position information of the detected light point;
    specifying a determination region where a specific defect is expected to be formed and a reference region which is a given region other than the determination region in the light point map, and calculating a ratio of a light point density of the determination region to a light point density of the reference region; and
    determining whether or not the specific defect is formed based on the calculated ratio.

8. The method of detecting a specific defect according to claim 7, further comprising a step of creating an overlap light point map obtained by overlaying light point maps of a plurality of wafers having the same shape onto one another,
    wherein the ratio is calculated in the calculation step using the overlap light point map instead of using the light point map.

9. A system for detecting a specific defect, comprising:
    a detection unit for detecting a defect on a surface of a wafer as a light point by irradiating the surface of the wafer with light;

an analysis unit for creating a light point map which is in-plane position information of the light point on the surface of the wafer based on output from the detection unit;
a storage unit for storing data on a determination region where a specific defect is expected to be formed and a reference region which is a given region other than the determination region in the light point map;
a calculation unit for calculating a ratio of a light point density of the determination region to a light point density of the reference region in the light point map; and
a determination unit for determining whether or not the specific defect is formed based on the calculated ratio.

* * * * *